United States Patent [19]

Tuke et al.

[11] Patent Number: 5,800,438
[45] Date of Patent: Sep. 1, 1998

[54] SURGICAL TOOL

[75] Inventors: Michael Antony Tuke, Guildford; Robert Michael Wozencroft, Surbiton, both of United Kingdom

[73] Assignee: Finsbury (Instruments) Limited, Leatherhead Surrey, United Kingdom

[21] Appl. No.: 735,033

[22] Filed: Oct. 22, 1996

[30] Foreign Application Priority Data

Oct. 23, 1995 [GB] United Kingdom ............ 9521683

[51] Int. Cl.$^6$ ........................................... A61B 17/56
[52] U.S. Cl. ........................................ 606/90; 606/102
[58] Field of Search ................... 606/86, 87, 88, 606/89, 90, 102; 33/810, 811, 812

[56] References Cited

U.S. PATENT DOCUMENTS

| | | |
|---|---|---|
| 3,200,501 | 8/1965 | Keszler ................. 33/812 |
| 5,116,338 | 5/1992 | Poggie et al. ........... 606/90 |
| 5,213,112 | 5/1993 | Niwa et al. ............. 128/774 |
| 5,468,244 | 11/1995 | Attfield et al. ......... 606/90 |
| 5,540,696 | 7/1996 | Booth, Jr. et al. ...... 606/88 |
| 5,630,820 | 5/1997 | Todd ................... 606/90 |

FOREIGN PATENT DOCUMENTS

| | | |
|---|---|---|
| 200822 | 8/1924 | United Kingdom. |
| 947325 | 1/1964 | United Kingdom. |
| 1058398 | 2/1967 | United Kingdom. |
| 1333668 | 10/1973 | United Kingdom. |
| 1391345 | 4/1975 | United Kingdom. |

OTHER PUBLICATIONS

Protek AG, a Company of Sulzermedica, "SICOT 90 Edition—F/S Modular Total Knee Replacement System", by M.A.R. Freeman and K.M. Samuelson, Reference Guide, 1990.

Protek AG, a Company of Sulzermedica, "F/S Modular System", Parts and Accessory Catalog, 1990.

*Primary Examiner*—Michael Powell Buiz
*Assistant Examiner*—David O. Reip
*Attorney, Agent, or Firm*—Senniger, Powers, Leavitt & Roedel

[57] ABSTRACT

The present invention relates to a surgical tool for use in knee arthroplasty. The tool is designed to assist a surgeon to implant a knee prosthesis which will be stable when the knee is in flexion and in extension. The tool comprises a parallel pair of paddle flanges adapted for insertion into the flexion or extension gap located between resected surfaces of a proximal tibia and a corresponding distal femur. The paddle flanges are incrementally movable relative to each other to define a range of gaps extending between a minimum gap and a maximum gap between exterior surfaces thereof. The incremental movement is provided by a racked member on which one of the paddle flanges is mounted, the racked member being movable by hand operable means connected thereto and which racked member engages with a pawl to prevent movement thereof in a gap-decreasing direction when the tool is in use.

26 Claims, 5 Drawing Sheets

SURGICAL TOOL

BACKGROUND OF THE INVENTION

The present invention relates to a surgical tool for use in knee arthroplasty.

Knee replacement operations have become increasingly common in recent years and are used to provide relief, for example, to patients having painful or debilitating conditions such as rheumatoid arthritis.

In knee arthroplasty, a surgeon cuts bone from the proximal tibia and the distal femur in order to accommodate in the resected joint a knee prosthesis having a femoral and a tibial component. The tibial component typically comprises a polyethylene seat having two wells for receiving the lateral and medial femoral condyles. When the knee is in full extension, it is the distal femoral condyles which are seated in the polyethylene wells. When the knee is in full flexion, the polyethylene wells receive the posterior femoral condyles. The polyethylene seat is usually mounted on a tibial plate made, for example, of titanium, a titanium alloy or a cobalt/chromium alloy which itself is anchored in the tibia.

The femoral component comprises a unitary body having a highly polished distal surface shaped to resemble the articulating surface of the distal femur, the articulating surface comprising lateral and medial pairs of condyles which extend anteriorly, posteriorly and distally. The prosthetic femoral component body is made, for example, of a cobalt/chromium alloy and has a proximal surface shaped to receive a distal femur which has been resected by the surgeon. Optionally, the femoral component is anchored to the femur by means of proximal anchoring stems and cement. The femoral component usually has a substantially uniform thickness over its condyles measured in an anterior-posterior plane.

Of the four or five bone cuts made by the surgeon depending upon the design of the knee implant, three or four are made on the distal femur and one on the proximal tibia. Of these cuts, three are crucial determinants of the gaps formed between the tibia and the femur when the resected knee joint is in flexion and in extension respectively and the collateral ligaments are taut, or at least the medial one thereof is taut.

For the prosthetic knee to be stable both in flexion and in extension, the gap between the resected bone surfaces in flexion ("the flexion gap") should be equal, as nearly as possible, to the gap between the said surfaces in extension ("the extension gap"). This is because the thickness of the femoral component is the same in both the flexion position and the extension position. The thickness of the tibial component remains the same in both positions. Hence the combined thickness of the two components is the same in both positions and should be equivalent in each case to the relevant thickness of the bone that has been resected. The gaps in the resected knee in flexion and extension, when the collateral ligaments are taut, should also be the same. The ligaments will then be equally taut both in flexion and extension when a suitable prosthesis is implanted. This will ensure knee stability and a full range of motion. If the flexion gap exceeds the extension gap and an implant is fitted that fills the flexion gap, the knee will be incapable of full extension. If the extension gap exceeds the flexion gap with a particular implant, then the knee will hyper-extend and will be unstable in full extension. Conversely, if an implant is fitted in this situation that fills the extension gap, there will be similar problems in flexion and risk of dislocation. If the relationship between the flexion and extension gaps is incorrect, the problem cannot be solved by altering the level of the tibial cut or by altering the thickness of the tibial prosthesis. These alterations would affect both the flexion and extension gaps equally. However, adjustment of the level of the distal femoral surface alters only the extension gap. Such adjustment can be made either by cutting bone from the distal femoral condyles or, in the other direction, by packing the surface of the distal femoral condyles with bone cement.

In practice, prosthetic implant thicknesses are chosen to fit in full extension. The surgeon, having cut bone from the proximal tibia and distal femur surfaces, inserts a series of prosthetic tibial implants of increasing thickness into the knee in flexion. He then brings the knee into full extension to check that the knee is stable in extension. If the flexion gap exceeds the extension gap, the distal femur can be progressively cut to allow the knee to extend fully and to be stable in flexion. If the extension gap exceeds the flexion gap then the surgeon can pack the distal femur with cement to close up the extension gap. Inevitably, the position of the cuts and the final choice of the thickness of the implants by the surgeon in these instances are somewhat haphazard because the choice of location of cut or level of pack is no more than an experienced estimate on the part of the surgeon.

In the past, surgeons have used two techniques to try to ensure that the knee is stable in flexion and extension. The more elaborate prior art technique involves the use of a device known as a tensor. This device comprises a fixed distal paddle having lateral and medial flanges and a pair of proximal paddles which are movable with respect to the distal paddle. The arrangement corresponds to a medial paddle pair and a lateral paddle pair. The upper, or proximal, paddles are mounted independently of each other. Movement of the respective proximal paddle is achieved by means of manually operable screw threads. When a winding handle is turned, the threaded portion of the corresponding arm moves up or down. The tensor is equipped with a measuring device for measuring the distance between the proximal and distal paddles recording it for future reference.

In use, the surgeon makes at least two bone cuts before using the tensor. These are to the proximal tibia and to the posterior femoral condyles. Then, with the knee in flexion, the surgeon inserts the tensor paddles, with the proximal and distal paddle pairs close together. Then, by turning the winding handle, he adjusts the proximal/distal paddle distance until it corresponds to the medial flexion gap with the collateral ligament taut. Repeating this process with the lateral paddle pair and having thus established the flexion gap, the surgeon adjusts the position of the recording device to measure the space between the bone cuts. He then locks the measuring device in position to record that distance. The paddles are then brought together to release the tensor from the knee. The knee is then brought into full extension, at which point the tensor is reinserted and anchored within the extension gap by opening the paddles again. The measuring device, still recording the flexion gap distance, is then used as a guide to mark the distal femur at a location where that portion of the bone may then be cut to provide an extension gap of equal magnitude to the flexion gap.

The tensor technique is in practice somewhat elaborate and difficult to use. It is not widely used by surgeons despite having been available since 1976.

The second technique, which is in fact widely used by surgeons, involves the use of simple spacers. These are metal plates of varying thicknesses which the surgeon can insert into the extension gap having already cut the proximal tibia and distal femur. These spacers are used as no more than a convenient checking device to confirm that the surgeon has cut enough bone to accommodate the prosthetic implant and to tell him what size of implant will fit one of the gaps, or perhaps both, without certainty nor control.

Prosthetic implants are manufactured in various sizes to fit various bone sizes. The combined thickness of the femoral and tibial components of such implants is chosen to match the flexion/extension gap which the surgeon has cut. Generally, the femoral prosthetic component is manufactured with a standard thickness of about 9 mm. Tibial components are manufactured in a variety of discrete thicknesses, beginning with about 7 mm and rising in approximately 2.5 mm increments to about 17 mm. Accordingly, the combined thickness of commercially available knee prostheses ranges from about 16 mm up to about 26 mm in approximately 2.5 mm increments.

If insufficient bone has been removed, the surgeon can cut additional bone away. If too much bone has been removed, the surgeon can select a larger prosthesis and then remove more bone if necessary to accommodate the larger thickness. Alternatively, an over-cut bone surface can be packed with an appropriate thickness of bone cement.

This method has the advantage of being simple, if reliable bone landmarks are used to judge the cuts. However, a common practice amongst surgeons is to use such spacers to measure the extension gap and not to go on to check that the flexion gap is of similar magnitude. In part this is due to uncertainty of what corrective action to take if the gaps are unequal. Accordingly, spacers have the disadvantage that, as surgical practice has developed, very little attention is paid to the flexion gap. This results in poor flexion or undue laxity of flexion with consequent risk of dislocation.

SUMMARY OF THE INVENTION

It is therefore an object of the present invention to provide surgeons with a means easily to check the relationship between the flexion and extension gap during knee arthroplasty without the need to become involved with elaborate and complicated techniques. It is a further object of the present invention to provide an operative aid which, during the course of an operation, provides instruction to a surgeon regarding the magnitude of a particular cut or pack which a surgeon should make to stabilise the flexion/extension gap relationship, and to identify the bone from which the cut should be taken or to which the pack should be applied. Yet a further object of the present invention is to provide a tool which assists a surgeon correctly to establish the extramedullar alignment of the leg during a knee replacement operation.

Accordingly, the present invention provides a surgical tool for checking the flexion and extension gaps located between previously resected surfaces of a proximal tibia and corresponding posterior and distal femoral condyles during knee arthroplasty, the tool comprising a central body portion from which extends a handle; a first paddle flange adapted for insertion into a flexion or extension gap, the first paddle flange being mounted on the central body portion; a second paddle flange substantially parallel to the first paddle flange and cooperating therewith in a first position to define, between an upper surface of an upper one of said first and second paddle flanges and a lower surface of a lower one of said first and second paddle flanges, a first distance corresponding to a minimum gap and movable relative to the first paddle flange to define a second distance between the said upper surface and the said lower surface corresponding to a maximum gap; the second paddle flange being mounted so as to be movable relative to the central body portion of the tool to vary the gap defined by the first and second paddle flanges; hand operable means arranged to cause movement of the second paddle flange in a gap-increasing direction to enable determination of the size of the flexion gap or the extension gap; and means providing to a surgeon using the tool indicia comparative of the size of the flexion or extension gap being checked with the size of a flexion or extension gap checked in a previous operation of the tool and/or indicative of any action to be taken to equalize the flexion or extension gap being checked with a flexion or extension gap checked in a previous operation of the tool.

In a particularly preferred form the surgical tool of the invention has the second paddle flange mounted on a racked member so as to be incrementally movable relative to the first paddle flange and wherein a pawl means is arranged to engage the racked member to prevent movement thereof in a gap-decreasing direction, which pawl means is releasable to allow the racked member to move freely between positions corresponding to the minimum and maximum gaps respectively.

Conveniently, the racked member is biased relative to the central body portion towards a position at which a minimum gap is defined between the first and second paddle flanges. In this case, the bias of the racked member may be provided by a coil spring bearing on the central body portion of the tool.

In a preferred embodiment, the racked member is arranged such that successive operation of the hand operable means connected to the member causes the racked member to move incrementally from a first end position corresponding to a minimum gap through a number of intermediate positions corresponding to intermediate gaps to a second end position corresponding to a maximum gap. Preferably, the incremental increase in the gap defined by the first and second paddle flanges upon successive operation of the hand operable means connected to the racked member corresponds to the incremental increase in successive thicknesses of knee prostheses. For example, the increment could be between about 0.5 mm and about 5 mm. The current increment in commercially available prostheses is typically about 2.5 mm.

The hand operable means connected to the racked member conveniently comprises a lever arm pivotally connected to the central body portion and operatively connected to the racked member, whereby pivotal motion of the lever arm relative to the central body portion causes motion of the racked member. In this case, the lever is preferably operable by the extended fingers of one hand, the same hand being used to grip the handle in its palm. The handle may be adapted to receive an extramedullary alignment bar whereby the surgeon, having inserted the tool paddle flanges into a patient's extension gap and having secured the tool in place by operating the hand operable means associated with the racked member to open the first and second paddle flanges to correspond to the patient's extension gap, can align the bar with respect to the handle and, bringing the end of the bar towards the hip, check the valgus angle of the femur with respect to the tibia. A convenient way of achieving this end is to provide a groove in the handle to receive the extramedullary alignment bar.

Visual indicia for indicating, in use, the magnitude of the gap defined by the first and second paddle flanges may be displayed on a member connected to the racked member and movable in association therewith. Preferably, the visual indicia are visible only through a window in an indicia housing section of the tool.

It is preferable if a datum line is visible on the housing section so that indicia displayed in the window align with the datum line to indicate, in use, the magnitude of the gap. More preferably, the indicia housing section carries, above and/or below the window, instructive information with respect to an operation being performed by the surgeon. Even more preferably, the indicia housing carries the instruction "cut" above the window and the instruction "pack" below the window to inform the surgeon, when using the tool to measure a patient's extension gap, having previously used the tool to measure the patient's flexion gap and having aligned a particular visible indicium with the centre of the window during that flexion gap measurement, that if that particular visible indicium is displayed above the centre of the window during extension gap measurement, the surgeon should cut more bone from the distal femur because the extension gap is too small, or that if that particular visible indicium is displayed below the centre of the window during extension gap measurement, the surgeon should pack the distal femur with cement because the extension gap is too large.

The racked member may comprise a racked shaft which extends from the distal paddle flange. Preferably, the racked shaft extends upwardly through the central body portion and into a housing column secured to the central body portion. In this case, the visual indicia may be provided on a sheath connected to the shaft. Preferably this sheath is rotatable relative to the shaft to display a selected one of a number of alternative indicia columns.

The pawl means may comprise teeth on an operating button or pin mounted in the central body portion of the tool, which teeth engage corresponding teeth on the racked member to prevent movement thereof in the direction specified. In this case it is preferred that the operating button or pin is biased into ratchet-type engagement with the racked member, but which engagement is releasable by manually urging the button or pin against its bias.

It can be arranged that each successive operation of the hand operable means associated with the racked member causes the pawl means to click onto the next successive tooth on the racked member, which click is audible, whereby the surgeon knows the magnitude of the flexion or extension gap according to the number of clicks he has heard.

In order that the invention may be properly understood and fully carried into effect, a preferred embodiment will now be described with particular reference to the accompanying drawings, wherein:

DETAILED DESCRIPTION OF THE PREFERRED EMBODIMENT

Figure 1:
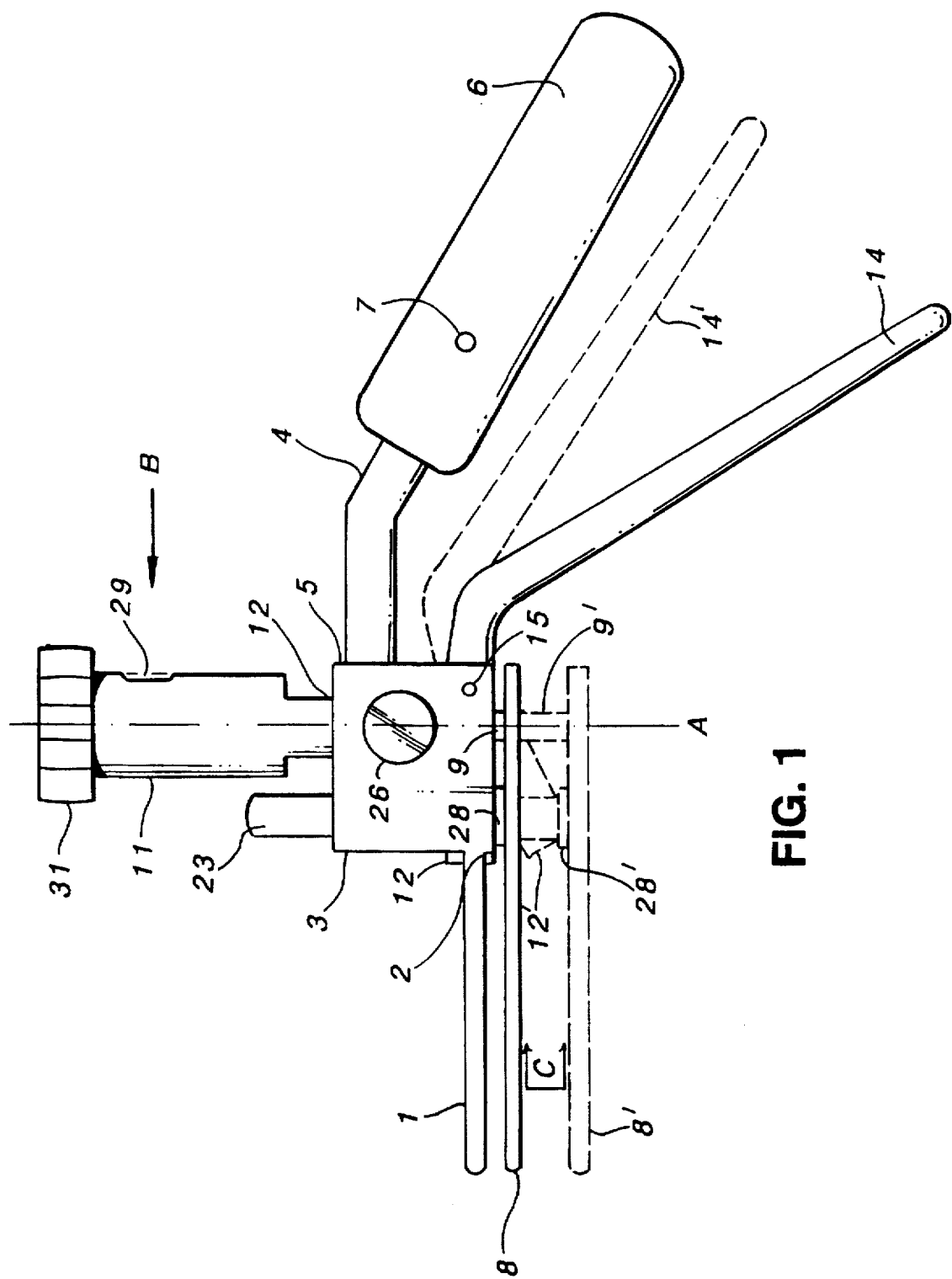
FIG. 1 shows a detailed side view of a surgical tool according to the invention.

Referring to FIG. 1, the surgical tool has a first, or proximal, stainless steel paddle flange 1 connected at weld seal 2 to stainless steel central body portion 3 of the tool. Stainless steel arm 4 extends from central body portion 3 and is attached thereto at weld seal 5. Arm 4 terminates in a handle 6 of metal or plastics material, which is secured to arm 4 by pin 7.

A second, or distal, stainless steel paddle flange 8 is mounted on stainless steel shaft 9 and both are movable downwardly to a lower position indicated in ghosted lines and by reference numerals 8' and 9' to show that shaft 9, and hence paddle flange 8, can move between their respective upper positions indicated at 8 and 9 and their respective lower positions 8' and 9' as indicated in FIG. 1. Shaft 9 is only just visible when paddle flange 8 is in its uppermost position. Shaft 9 extends upwardly through bore 10 (FIG. 2) in central body portion 3 into stainless steel column 11. Column 11 is attached to central body portion 3 at weld seal 12. Shaft 9 is movable within central body portion 3 but is biased towards its uppermost position by coil spring 13 (FIG. 2) located inside column 11. Movement of shaft 9, and hence of distal paddle flange 8, is controlled by means of stainless steel lever 14 which is shown in FIG. 1 in two alternative positions 14 and 14'. Lever 14 is pivotally connected to central body portion 3 by pin 15. Lever 14, as shown in solid outline, extends through central body portion 3 and can be seen protruding slightly from the end of central body portion 3 near the junction thereof with proximal paddle flange 1. Proximal paddle flange 1 is provided with recess 16 (FIG. 10) to accommodate the protruding end of lever 14.

Figure 3:
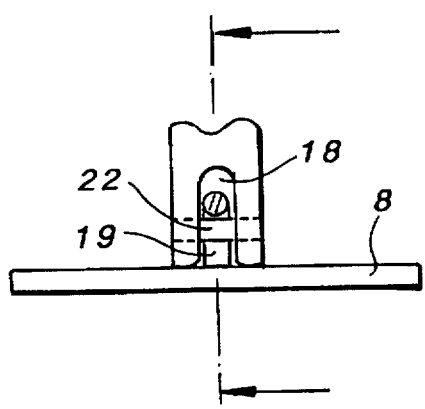
FIG. 3 shows a front end view of a small section of the tool when viewed along arrow C of FIG. 1.
Figure 4:
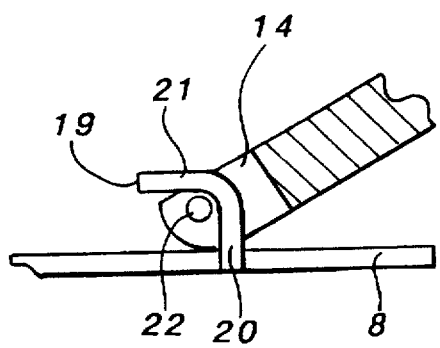
FIG. 4 shows a side sectional view of the portion of the tool depicted in FIG. 3.
Figure 5:
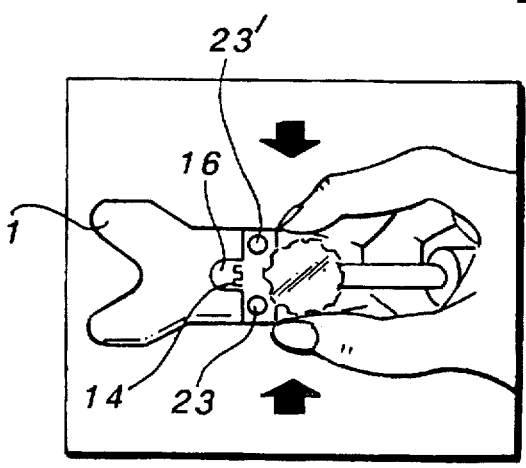
FIG. 5 shows a perspective view of a portion of the tool with the central body portion removed for clarity.

Referring to FIGS. 3, 4 and 5, lever 14 has a vertical slot 17 through which shaft 9 extends. The protruding end of lever 14 has a groove 18 which receives a retaining pin 19 mounted on distal paddle flange 8. Retaining pin 19 is of inverted L-shape with a vertical portion 20 extending upwardly from distal paddle flange 8 into the grooved end 18 of lever 14 and a horizontal portion 21 extending towards paddle flanges 1 and 8. The retaining pin 19 receives in its crook a transverse bar 22 mounted within the end groove 18 of lever 14.

Referring again to FIG. 1, on distal paddle flange 8 are mounted two stainless steel guide poles, one of which is designated by reference numeral 23 in FIG. 1. The second guide pole 23' (visible in FIG. 10) is directly behind guide pole 23 as the tool is viewed in FIG. 1. Guide poles 23 and 23' extend upwardly through vertical bores (not shown) in central body portion 3. A snug but slidable fit between each guide pole 23 and its respective bore ensures that movable distal paddle flange 8 always maintains a stable and parallel aspect with respect to fixed proximal paddle flange 1.

Shaft 9 has, within central body portion 3, a ratchet surface 24 (FIG. 2) which engages with pawl teeth 25 (FIG. 2) on stainless steel operating button 26. Button 26 is biased by means of coil spring 27 (FIG. 2) located in a recessed interior portion of central body portion 3. Coil spring 27 biases pawl teeth 25 of operating button 26 into engagement with ratchet surface 24 of shaft 9, thus preventing shaft 9 from moving upwardly to close the gap between paddle flanges 1 and 8. Button 26 can be manually pressed against the bias of coil spring 27 to release the ratchet mechanism and allow shaft 9 to slide freely inside central body portion 3 between limits defined by an upward stop 28 (shown in FIG. 1 as 28' in its lower position) which prevents distal paddle 8 from engaging proximal paddle 1, and defines a gap of 11 mm between the lower (distal) surface of paddle 8 and the upper (proximal) surface of paddle 1, and a downward stop 47 (FIG. 2) located inside column 11.

Figure 6:
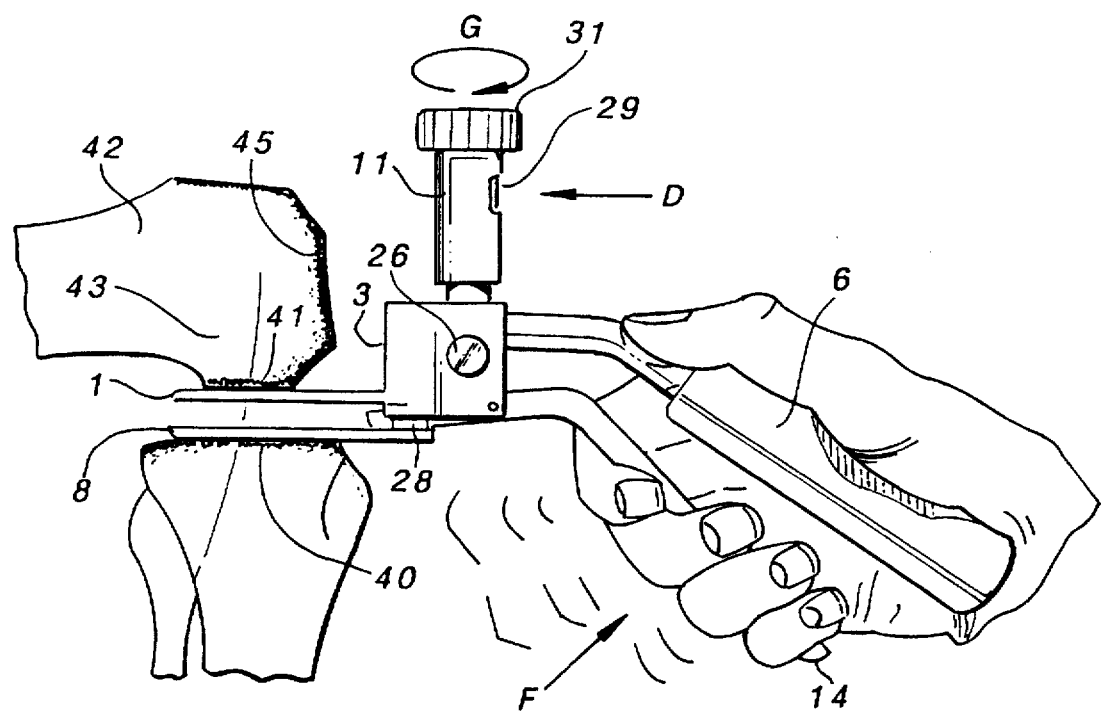
FIG. 6 shows a side view of the tool of FIG. 1 being used to determine the flexion gap in a resected knee.
Figure 8:
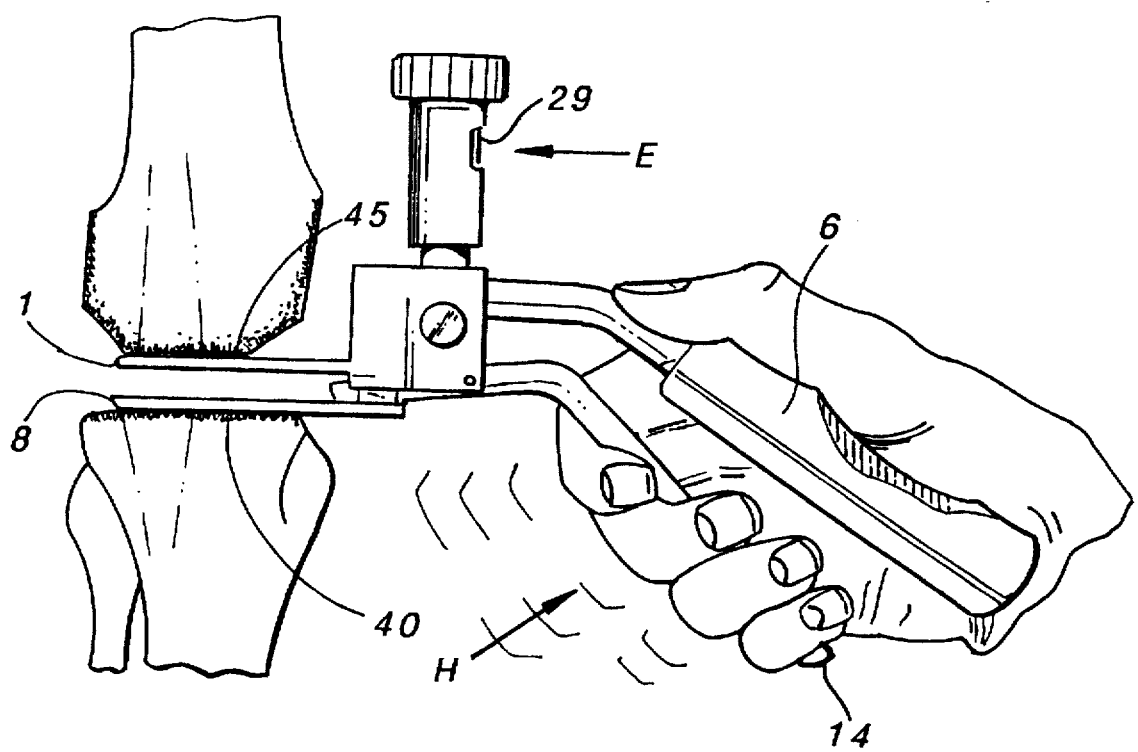
FIG. 8 shows a similar view of the tool of FIG. 1 being used to determine the extension gap in a resected knee.

Column 11 is fixed relative to central body portion 3 and has a window 29 through which visible indicia shown in FIGS. 6 and 8 mounted inside column 11 can be viewed. The visible indicia are provided on stainless steel sheath 30 (FIG. 2) within column 11, which sheath is operatively connected to shaft 9 to move vertically in response to vertical movement of shaft 9 and display different respective indicia in window 29 as a result of such movement. Sheath 30 is also rotatable, rotation being manually effected by means of stainless steel knob 31. Four columns of visible indicia are carried by sheath 30, each respective column being accessible in one of four sheath positions defined by knob 31. Two opposing guide pins 32 and 32' (FIG. 2) are located in knob 31 and retain the knob in position by seating in accommodating recesses 33 and 33' (FIG. 2), of which there are four at 90° intervals, around the top of column 11.

Figure 2:
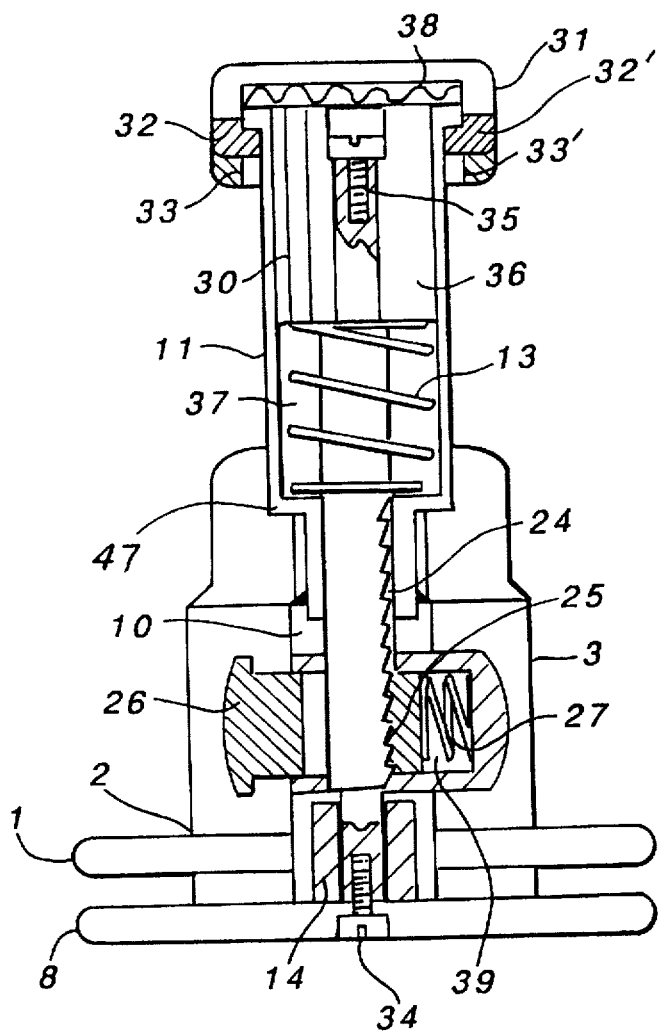
FIG. 2 shows a cross-sectional drawing through line A—A of FIG. 1 when viewed in the direction indicated by arrow B.

In FIG. 2, the mechanism of the tool inside central body portion 3 and column 11 is more particularly displayed by means of a cross-sectional drawing, which is a cross-section taken through line A—A on FIG. 1 and viewed in the direction of arrow B. Proximal paddle flange 1 is attached to central body portion 3 at weld seal 2. Distal paddle flange 8 is mounted beneath paddle flange 1 and is stably but slidably secured in parallel relation thereto by guide poles 23 and 23' which extend vertically through respective bores (not shown) in central body portion 3. Shaft 9 is secured to paddle flange 8 by threaded screw 34. Reference numeral 14 indicates lever 14 which has a vertical slot 17 (FIG. 5) to receive shaft 9 therethrough. Shaft 9 extends upwardly vertically through central body portion 3 into column 11.

The top of shaft 9 is secured by screw thread 35 to carriage 36, which carriage 36 is vertically movable within housing 37. Carriage 36, and hence shaft 9, are urged towards an uppermost position within housing 37 by coil spring 13. Visible indicia sheath 30 is also mounted on carriage 36 but is rotatable relative thereto by rotation of knob 31. Knob 31 has two guide pins 32 and 32' which are seated in recesses 33 and 33' at the top of column 11. There are four such recesses at 90° intervals around the top of column 11. Resilient washer 38 ensures that guide pins 32 are urged into seating engagement with recesses 33. Shaft 9 has a racked surface 24 which engages teeth 25 on operating button 26. The ratchet engagement can be released by pressing on operating button 26 to urge it into recess 35 within central body portion 3.

Figure 7:
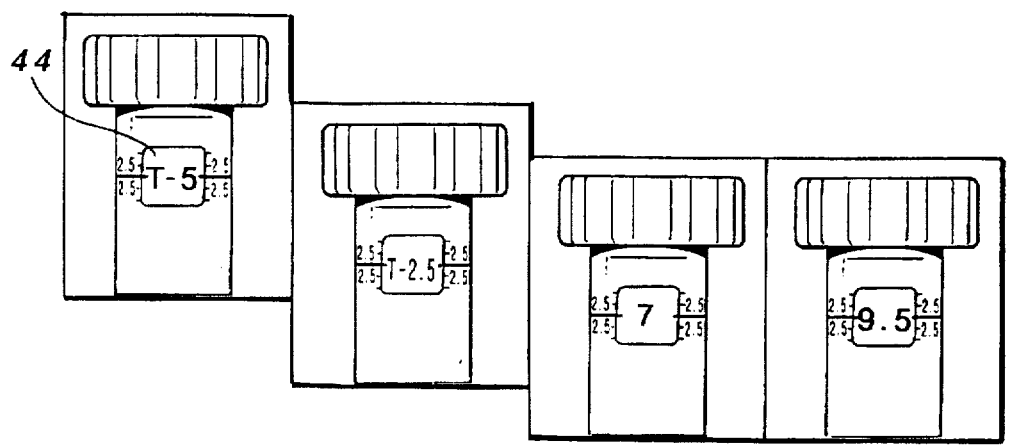
FIG. 7 shows a series of possible views of visible indicia on the tool viewed along arrow D of FIG. 6 during flexion gap measurement.

In use, referring to FIGS. 6 and 7, a surgeon first presses operating button 26 to release shaft 9 from its ratchet lock whilst being careful to avoid squeezing lever 14 and handle 6 together. Shaft 9 can then move upwardly under the influence of the coil spring 13 within column 11, to which shaft 9 is connected. This movement brings distal paddle flange 8 into its closest possible proximity with proximal paddle flange 1 with stop 28 determining the gap between the two paddle flanges. This gap is predetermined such that the total distance from the proximal (upper) surface of proximal paddle flange 1 to the distal (lower) surface of distal paddle flange 8 is 11 mm. This corresponds to a flexion gap of 5 mm less than that required by the smallest commercially available prosthetic implant, which has a tibial component 7 mm in depth and a femoral component of 9 mm thickness. The prosthesis is thus 16 mm in total depth. Before inserting the tool, the surgeon cuts bone from the proximal tibia and the distal femur in an amount which he estimates will yield an approximately correct gap in flexion and extension for the particular prosthesis he has selected as being suitable for his patient. He then inserts paddle flanges 1 and 8 into the flexion gap, i.e. the gap defined between the proximal tibia resected bone surface 40 and the resected posterior condyles 41 on the distal femur 42 when the knee is in flexion. Then, by squeezing lever 14 towards handle 6 in the direction indicated by arrow F, the surgeon lowers shaft 9, and hence distal paddle flange 8. Gentle pressure on lever 14 causes pawl teeth 25 (FIG. 2) on operating button 26 to click onto the next tooth on racked shaft 9. This click is audible and the number of clicks made thus gives the surgeon a very approximate indication of the magnitude of the flexion gap. The rack is arranged such that each respective click causes the flexion gap defined by the proximal and distal paddle flange surfaces to increase by about 2.5 mm, corresponding to the increments in which prosthetic implants are commercially available. The surgeon continues to squeeze lever 14 until the paddle flanges are open to their fullest extent possible within the flexion gap, with the collateral ligaments 43 taut. One advantage of the present invention is that the surgeon can readily judge the degree of resistance within the joint to any further ratchet click which he may feel it correct to make.

Figure 9:
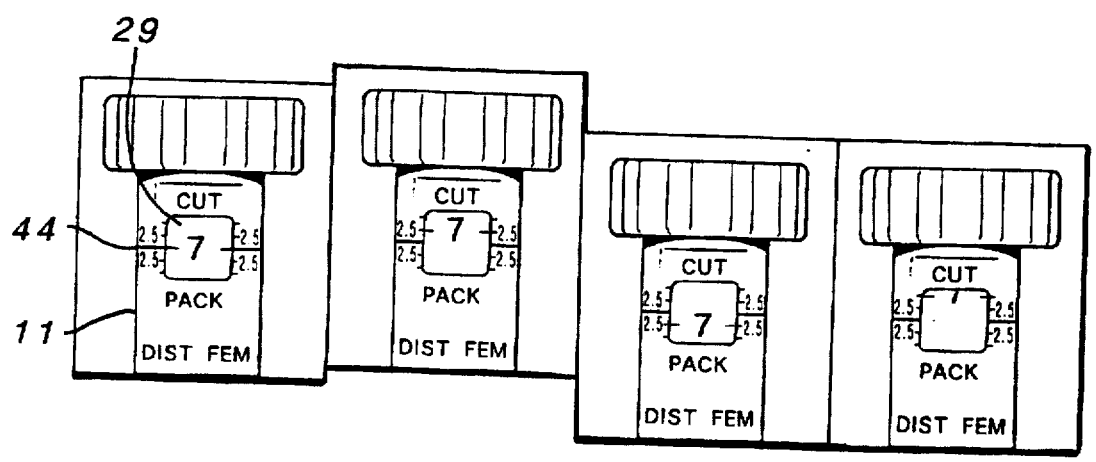
FIG. 9 shows a series of possible views of visible indicia on the tool viewed along arrow E of FIG. 8 during extension gap measurement.

Having thus adjusted proximal and distal paddle flanges 1 and 8 to correspond, between their respective proximal and distal surfaces, to the magnitude of the flexion gap in the resected joint, the surgeon rotates knob 31 in the direction indicated by arrow G until one of seven possible visible indicia is displayed in the centre of window 29 as viewed along arrow D. FIG. 7 shows four of the seven possible indicia. If "T-5" is displayed in window 29 opposite datum line 44 that circumscribes column 11, as shown in FIGS. 7 and 9, the surgeon knows that the flexion gap is too small to allow even the smallest commercially available prosthetic implant to be accommodated therein and that a further 5 mm of bone should be cut to allow the smallest implant to be used. Assuming the surgeon has cut approximately equal amounts of bone from the posterior and distal femur condyles 41 and 45 respectively, the extra 5 mm should be cut from the tibia (hence "T-5"). This is because only a further tibia cut will increase both the flexion and extension gaps simultaneously.

If "T-2.5" is displayed in window 29 opposite datum line 44, the surgeon is informed that he should cut a further 2.5 mm off the proximal tibia in order to use the smallest prosthetic implant.

If "7", "9.5", "12", "14.5", or "17" are displayed in window 29 opposite datum line 44, the surgeon knows that the gap he has cut is wide enough to accommodate an implant having a total depth on its tibia component of 7, 9.5, 12, 14.5 or 17 mm respectively.

When the surgeon is satisfied that the flexion gap is of appropriate magnitude, he releases the tool from the joint by pressing on operating button 26. This action urges the operating button pawl teeth 25 (FIG. 2) into recessed area 39 (FIG. 2) inside central body portion 3, thus releasing the teeth from their ratchet-type engagement with ratchet surface 24 (FIG. 2) of shaft 9. Shaft 9 is then urged, by coil spring 13 (FIG. 2) within column 11, towards its uppermost position, thus bringing distal paddle flange 8 back into its closest possible proximity to paddle flange 1.

The surgeon then releases the tool from the joint whilst leaving knob 31 in the same position at which the flexion gap was displayed in the centre of window 29 during the first measurement. Then, and now referring to FIGS. 8 and 9, after moving the knee into full extension, the surgeon reinserts the tool into the extension gap defined between the resected proximal tibia 40 and distal femur condyles 45. He then squeezes lever 14 towards handle 6 in the direction indicated by arrow H until paddle flanges 1 and 8 separate to correspond to the extension gap. If the same visible indicium is displayed in the centre of window 29 opposite datum line 44 as was displayed during flexion gap measurement ("the flexion indicium"), the surgeon knows that the flexion and extension gaps are approximately equal and he can proceed to implant the prosthesis. If the flexion indicium remains above the centre of window 29, the surgeon knows that the extension gap is too small and he must cut a certain amount of bone off the distal femur condyles. If the flexion indicium falls below the centre of window 29, the surgeon knows that the extension gap is too large and he must pack the distal femur with a certain quantity of bone cement. The indicia can be arranged to display how much bone needs to be removed from, or alternatively, what thickness of bone cement needs to be packed onto the distal femur. Thus, in the embodiment depicted in FIG. 9, the word "cut" is displayed on column 11 above window 29 and the word "pack" is displayed below window 29. The numerals "2.5" are displayed above and below the datum line 44 at the centre of window 29 to indicate that a further 2.5 mm of bone should be cut from the distal femur or, alternatively, that a 2.5 mm layer of bone cement should be packed onto the distal femur prior to implantation of the prosthesis.

Figure 10:
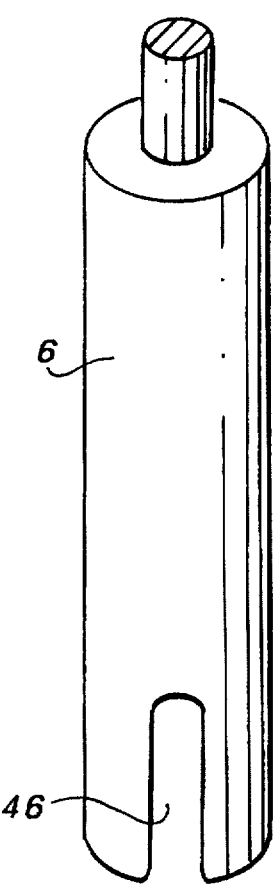
FIG. 10 shows a top view of part of the tool depicted in FIGS. 6 and 8.

FIG. 10 shows a top view of the same embodiment of the invention depicted in FIG. 1. This shows recess 16 in proximal paddle flange 1, which recess accommodates the protruding end of lever 14.

Figure 11:
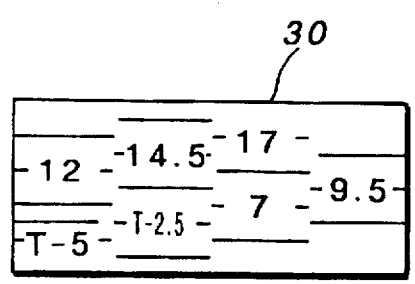
FIG. 11 shows a developed view of the indicia visible when the tool is viewed along arrow D of FIG. 6 or arrow E of FIG. 8.

FIG. 11 shows a developed view of visible indicia sheath 30, showing the seven alternative indicia viewable in the particular embodiment of the invention which has been described above.

Figure 12:
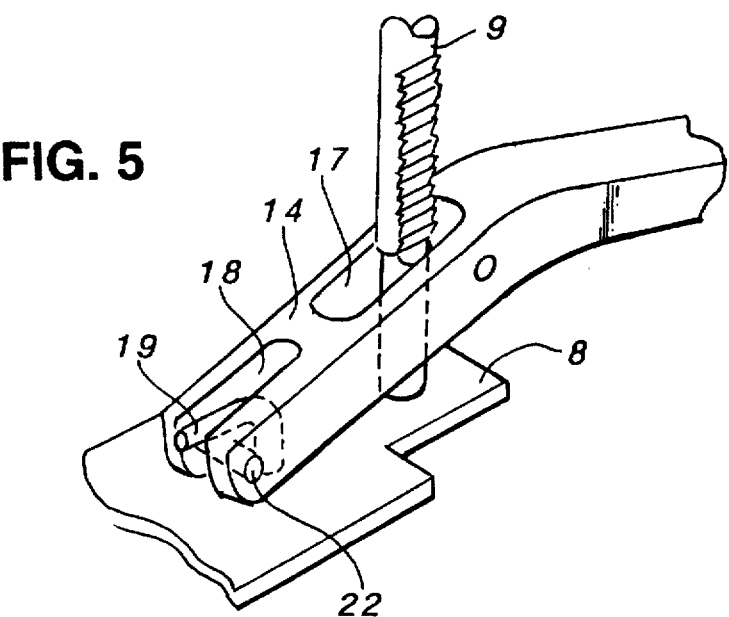
FIG. 12 shows a top plan view of the handle of the tool, indicating the presence of the extra- or intramedullary alignment groove.

FIG. 12 shows a top view of handle 6 in which groove 46 for accommodating an intramedullary or extramedullary alignment bar can be seen. Thus, in use, a surgeon may use such a bar to check the valgus angle between his patient's femur and tibia by aligning the bar in groove 46 while the surgical tool of the invention is securely seated in the resected joint with the knee in full extension.

An advantage of the tool of the present invention is that it allows a surgeon to use anterior referencing in the course of the operation. Normally it is necessary for the surgeon to use posterior referencing so that all measurements are made from the back of the knee which is less satisfactory. Because of the variation in physical size of patients they are likely to have differing bone sizes. However, only a limited range of sizes of knee implant is manufactured and sold. Often the gap between different thicknesses can be from about 4 mm to about 5 mm. The surgeon would ideally like to have as much metal as possible at the back of the knee. However, if he uses posterior referencing, any difference between an implant which would be a perfect fit and the next available larger size means that the implant may project somewhat at the front of the knee after implantation. This is currently the best way for the surgeon to achieve correct, or near correct, balance between the flexion gap and the extension gap. Above all the surgeon must avoid resecting the bone so far that he removes a part of the anterior cortex of the femur. If he does then there is a risk of fracture of the femur.

The present invention allows the surgeon to use anterior referencing, using the anterior cortex of the femur as a reference surface.

FIG. 7 illustrates a series of indicia including T-5 and T-2.5. These indications are appropriate only for an implant having a nominal thickness of 7 mm. If the surgeon decides to use a thicker implant, eg 9 mm implant, then he has to do some mental arithmetic to derive the correct information from the tool. If desired the indicia T-5, T-2.5 etc can be replaced by other types of indicia, for example a hatched area having horizontal lines drawn across it with spacings there between corresponding to the nominal increment between different thicknesses of implant in a particular manufacturer's range of implants.

We claim:

1. A surgical tool for checking the flexion and extension gaps located between previously resected surfaces of a proximal tibia and corresponding posterior and distal femoral condyles during knee arthroplasty, the tool comprising a central body portion from which extends a handle; a first paddle flange adapted for insertion into a flexion or extension gap, the first paddle flange being mounted on the central body portion; a second paddle flange substantially parallel to the first paddle flange and cooperating therewith in a first position to define, between an upper surface of an upper one of said first and second paddle flanges and a lower surface of a lower one of said first and second paddle flanges, a first distance corresponding to a minimum gap and movable relative to the first paddle flange to define a second distance between the said upper surface and the said lower surface corresponding to a maximum gap; the second paddle flange being mounted so as to be movable relative to the central body portion of the tool to vary the gap defined by the first and second paddle flanges; hand operable means arranged to cause movement of the second paddle flange in a gap-increasing direction to enable determination of the size of the flexion gap or the extension gap; and means providing to a surgeon using the tool indicia comparative of the size of the flexion or extension gap being checked with the size of a flexion or extension gap checked in a previous operation of the tool.

2. A surgical tool according to claim 1, wherein the second paddle flange is mounted on a racked member so as to be incrementally movable relative to the first paddle flange and wherein a pawl means is arranged to engage the racked member to prevent movement thereof in a gap-decreasing direction, which pawl means is releasable to allow the racked member to move freely between positions corresponding to the minimum and maximum gaps respectively.

3. A surgical tool according to claim 2, wherein the racked member in biased relative to the central body portion towards the first position at which a minimum gap is defined between the first and second paddle flanges.

4. A surgical tool according to claim 3, wherein the bias of the racked member is provided by a coil spring bearing on the central body portion of the tool.

5. A surgical tool according to claim 2, wherein the hand operable means is connected to the racked member and is arranged such that successive operation of the hand operable means causes the racked member to move incrementally from a first end position corresponding to the minimum gap through a number of intermediate positions corresponding to intermediate gaps to a second end position corresponding to the maximum gap.

6. A surgical tool according to claim 5, wherein the incremental increase in the gap defined by the first and second paddle flanges upon successive operation of the hand operable means connected to the racked member corresponds to the incremental increase in successive thicknesses of knee prostheses.

7. A surgical tool according to claim 6, wherein the incremental increase is from about 0.5 mm to about 5 mm.

8. A surgical tool according to claim 7, wherein said hand operable means is capable of increasing the gap between the first and second paddle flanges in increments of about 2.5 mm.

9. A surgical tool according to claim 2, wherein the hand operable means connected to the racked member comprises a lever arm pivotally connected to the central body portion and operatively connected to the racked member, whereby pivotal motion of the lever arm relative to the central body portion causes motion of the racked member.

10. A surgical tool according to claim 9, wherein the lever arm is operable by the extended fingers of one hand, the same hand being used to grip the handle in its palm.

11. A surgical tool according to claim 2, wherein said indicia providing means comprise visual indicia for indicating, in use, the magnitude of the gap defined by the first and second paddle flanges displayed on a member connected to the racked member and movable in association therewith.

12. A surgical tool according to claim 11, wherein the visual indicia are visible only through a window in an indicia housing section.

13. A surgical tool according to claim 12, wherein a datum line is visible on the housing section so that indicia displayed in the window align with the datum line to indicate, in use, the magnitude of the gap.

14. A surgical tool according to claim 12, wherein the indicia housing carries, above and/or below the window, instructive information with respect to an operation being performed by the surgeon.

15. A surgical tool according to claim 14, wherein the indicia housing carries the instruction "cut" above the window and the instruction "pack" below the window to inform the surgeon using the tool to measure a patient's extension gap, having previously used the tool to measure the patient's flexion gap and having aligned a particular visible indicium with the centre of the window, that if that particular visible indicium is displayed above the centre of the window during extension gap measurement, the surgeon should cut more bone from the distal femur because the extension gap is too small, or that if that particular visible indicium is displayed below the centre of the window during extension gap measurement, the surgeon should pack the distal femur with cement because the extension gap is too large.

16. A surgical tool according to claim 2, wherein the racked member is a shaft which extends from the second paddle flange.

17. A surgical tool according to claim 16, wherein the racked shaft extends upwardly through the central body portion and into a housing column secured to the central body portion.

18. A surgical tool according to claim 16, wherein visual indicia are mounted on a sheath connected to the shaft and which sheath is rotatable relative to the shaft to display a selected one of a number of alternative indicia columns.

19. A surgical tool according to claim 2, wherein the pawl means comprise teeth on an operating button or pin mounted in the central body portion of the tool, which teeth engage corresponding teeth on the racked member to prevent movement thereof in the said gap decreasing.

20. A surgical tool according to claim 19, wherein the operating button is biased into ratchet-type engagement with the racked member, but which engagement is releasable by manually urging the button against its bias.

21. A surgical tool according to claim 2, wherein each successive operation of the hand operable means associated with the racked member causes the pawl means to click onto a next successive tooth on the racked member, which click is audible, whereby the surgeon knows the magnitude of the flexion or extension gap according to the number of clicks he has heard.

22. A surgical tool according to claim 1, wherein the handle is adapted to receive extramedullary alignment bar whereby the surgeon, having inserted the tool paddle flanges into a patient's extension gap and having secured the tool in place by operating the hand operable means associated with the racked member to open the first and second paddle flanges to correspond to the patient's extension gap, can align the bar with respect to the handle and, bringing the end of the bar towards the hip, check the valgus angle of the femur with respect to the tibia.

23. A surgical tool according to claim 22, wherein the handle is provided with a groove to receive the extramedullary alignment bar.

24. A surgical tool according to claim 1, wherein said comparative indicia means is capable of giving simultaneous indications of the size of the flexion or extension gap being checked and the size of a flexion or extension gap checked in a previous operation of the tool.

25. A surgical tool according to claim 1, wherein the second paddle flange has a medial section and a lateral section which move in unison upon operation of the hand operable means.

26. A surgical tool according to claim 1, further comprising means providing to a surgeon using the tool indicia indicative of any action to be taken to equalize the flexion or extension gap being checked with a flexion or extension gap checked in a previous operation of the tool.

* * * * *